United States Patent
Mouradian et al.

(10) Patent No.: US 10,736,889 B2
(45) Date of Patent: *Aug. 11, 2020

(54) METHOD OF TREATING DYSKINESIA

(71) Applicant: Rutgers, The State University of New Jersey, New Brunswick, NJ (US)

(72) Inventors: M. Maral Mouradian, Princeton, NJ (US); Steven Braithwaite, Redwood City, CA (US); Michael Voronkov, Pennington, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/909,576

(22) Filed: Mar. 1, 2018

(65) Prior Publication Data

US 2018/0185355 A1 Jul. 5, 2018

Related U.S. Application Data

(63) Continuation-in-part of application No. 15/019,218, filed on Feb. 9, 2016, now Pat. No. 9,918,980, which is a continuation-in-part of application No. 14/113,340, filed as application No. PCT/US2012/035129 on Apr. 26, 2012, now Pat. No. 9,289,423.

(60) Provisional application No. 61/480,415, filed on Apr. 29, 2011.

(51) Int. Cl.
*A61K 31/485* (2006.01)
*A61P 25/14* (2006.01)
*A61K 45/06* (2006.01)

(52) U.S. Cl.
CPC ............ *A61K 31/485* (2013.01); *A61K 45/06* (2013.01); *A61P 25/14* (2018.01)

(58) Field of Classification Search
None
See application file for complete search history.

(56) References Cited

U.S. PATENT DOCUMENTS

| | | | |
|---|---|---|---|
| 5,750,534 A | 5/1998 | Yoa-Pu et al. | |
| 6,569,449 B1 | 5/2003 | Stinchcomb et al. | |
| 6,703,398 B2 | 3/2004 | Hu et al. | |
| 2002/0068692 A1* | 6/2002 | Willis | A61K 31/00 514/1 |
| 2003/0105120 A1 | 6/2003 | Hu et al. | |
| 2003/0149066 A1 | 8/2003 | Levine | |
| 2004/0186111 A1 | 9/2004 | Sun et al. | |
| 2005/0137141 A1 | 6/2005 | Hilfinger | |
| 2009/0030026 A1 | 1/2009 | Baichwal et al. | |
| 2009/0060871 A1 | 3/2009 | Voronkov et al. | |

FOREIGN PATENT DOCUMENTS

| | | | | |
|---|---|---|---|---|
| CA | 2822528 A1 | 7/2012 | | |
| CN | 1107333 A | 8/1995 | | |
| EP | 615756 A1 | 9/1994 | | |
| EP | 1149836 A1 * | 10/2001 | ........... | C07D 489/08 |
| EP | 2402005 A1 | 1/2012 | | |
| JP | 2002520362 A | 7/2002 | | |
| JP | 2003-506385 A | 2/2003 | | |
| JP | 2004-535419 A | 11/2004 | | |
| WO | 2002009768 A2 | 2/2002 | | |
| WO | 2005009377 A2 | 2/2005 | | |
| WO | 2007022535 A2 | 2/2007 | | |
| WO | 2007127683 A2 | 11/2007 | | |
| WO | WO 2007127683 A2 * | 11/2007 | ........... | A61K 9/2027 |
| WO | 2009092071 A2 | 7/2009 | | |
| WO | 2010112942 A1 | 10/2010 | | |
| WO | 2011007247 A1 | 1/2011 | | |
| WO | 2011083304 A1 | 7/2011 | | |
| WO | 2012089738 | 7/2012 | | |

OTHER PUBLICATIONS

De Souza et al. JPET, 1988 (244) 391-402; (Year: 1988).*
Korprich et al. Movment Disorders, 2011 (26) 1225-33 (in the IDS); (Year: 2011).*
Ikeda et al. Eur J Pharmacol, 2009 (620) 42-48 (in the IDS); (Year: 2009).*
Berg et al. J Neural Transm, 1999 (106) 725-28 (in the IDS). (Year: 1999).*
Errick et al. Drugs 1983 (26) 191-211 (in the IDS). (Year: 1983).*
Houde Br. J. clin. Pharmac. (1979), 7, 297S-308S (Year: 1979).*
Sawada et al. "Amantadine for Dyskinesias in Parkinson's Disease: A Randomized Controlled Trial," PLoS One 2010, 5(12):e15298. (Year: 2010).*
Wang, J. J. et al., "A Comparison Among Nalbuphine, Meperidine, and Placebo for Treating Postanesthetic Shivering," Anesthesia & Analgesia, Mar. 1999, vol. 88, No. 3, pp. 686-689 (Abstract).
Schmidt, William K. et al., Nalbuphine, Drug and Alcohol Dependence, 1985, vol. 14, pp. 339-362.
De Souza et al.: "Nalbuphine: An Autoradiographic Opioid Receptor Binding Profile in the Central Nervous System of an Agonist/Antagonist Analgesic", The Journal of Pharmacology and Experimental Therapeutics, 1988, vol. 244, No. 1, pp. 391-402.
Gunion, et al.: "Use of the Mixed Agonist-Antagonist Nalbuphine in Opioid Based Analgesia", Elsevier, 2004, vol. 6, pp. 29-39.
Aubert I. et al., "Enhanced preproenkephalin-B-derived opioid transmission in striatum and subthalamic nucleus converges upon globus pallidus internalis in L-dopa-induced dyskinesia" Biol Psychiatry, Apr. 2007, vol. 61, No. 7, pp. 836-844 (Abstract).
Aungst, B. et al., "Prodrugs for improved oral nalbuphine bioavailability: inter-species differences in the disposition of nalbuphine and its acetylsalicylate and anthranilate esters," International Journal of Pharmaceutics Aug. 1987, vol. 38, issues 1-3, pp. 199-209 (Abstract).
Benyamin R, et al. "Opioid Complications and Side Effects," Pain Physician 2008, Opioid Special Issue: vol. 11, pp. S105-S120.

(Continued)

*Primary Examiner* — Jeffrey S Lundgren
*Assistant Examiner* — Michael J Schmitt
(74) *Attorney, Agent, or Firm* — Cooley LLP (57) ABSTRACT

Methods of treating patients with dyskinesias, by administering a therapeutically effective amount of a dual-action μ-opioid receptor antagonist/κ-opioid receptor agonists or prodrug thereof to a subject in need thereof, sufficient to mitigate the dyskinesia. Alternatively, a combination of both a μ-opioid receptor antagonist or prodrug thereof, and a κ-opioid receptor agonist or prodrug thereof can be administered, either together or separately.

19 Claims, 2 Drawing Sheets

(56) References Cited

OTHER PUBLICATIONS

Berg D. et al., "Reduction of Dyskinesia and Induction of Akinesia Induced by Morphine in Two Parkinsonian Patients With Severe Sciatica," J Neural Transm, 1999, vol. 106, No. 7-8, pp. 725-728 (Abstract).
Bodnar, RJ, et al., "Endogenous Opiates and Behavior: 2001," Peptides, Dec. 2002, vol. 23, No. 12, pp. 2307-2365 (Abstract).
Borgeat, A. et al., "The effect of nalbuphine and droperidol on spontaneous movements during induction of anesthesia with propofol in children" J. of Clinical Anesthesia, Butterworth Publishers, Stoneham, GB, vol. 5, No. 1, 1993, pp. 12-15.
Brotchie, JM, "Nondopaminergic Mechanisms in Levodopa-Induced Dyskinesia," Mov Disord, 2005, vol. 20, No. 8, pp. 919-931 (Abstract).
Calon F., et al., "Increase of Preproenkephalin mRNA Levels in the Putamen of Parkinson Disease Patients With Levodopa-Induced Dyskinesias," J Neuropathol Exp Neurol, 2002, vol. 61, No. 2, pp. 186-196 (Abstract).
Cao X., et al., "Striatal Overexpression of Delta FosB Reproduces Chronic Levodopa-Induced Involuntary Movements," J Neuroscience, May 2010, vol. 30, No. 21, pp. 7335-7343.
Cao X., et al., "Blockade of Cannabinoid Type 1 Receptors Augments the Antiparkinsonian Action of Levodopa Without Affecting Dyskinesias in MPTP-Treated Rhesus Monkeys," J Pharmacol Exp Ther, 2007, vol. 323, No. 1, pp. 318-326.
Cenci, M.A. et al., "Maladaptive Striatal Plasticity in L-DOPA-Induced Dyskinesia," Prog Brain Res, 2010, vol. 183, pp. 209-233.
Cox H., et al., "The Selective Kappa-Opioid Receptor Agonist U50,488 Reduces L-Dopa-Induced Dyskinesias but Worsens Parkinsonism in MPTP-Treated Primates," Exp Neurol, 2007, vol. 205, No. 1, pp. 101-107.
Encarnacion, E. V., et al., "Levodopa-Induced Dyskinesias in Parkinson's Disease: Etiology, Impact on Quality of Life, and Treatments," European Neurology, vol. 60, No. 2, May 15, 2008, pp. 57-66.
Engber, TM, et al., "Levodopa Replacement Therapy Alters Enzyme Activities in Striatum and Neuropeptide Content in Striatal Output Regions of 6-Hydroxydopamine Lesioned Rats," Brain Res, Jun. 1991, vol. 552. No. 1, pp. 113-118 (Abstract).
Errick, JK and Heel, RC, "Nalbuphine. A Preliminary Review of its Pharmacological Properties and Therapeutic Efficacy," Drugs, Sep. 1983, vol. 26, No. 3, pp. 191-211 (Abstract).
Fabbrini, G, et al., "Levodopa-Induced Dyskinesias," Mov Disord, Jul. 2007, vol. 22, No. 10, pp. 1379-1389 (Abstract).
Fang J.Y., et al., "Transdermal Delivery of Nalbuphine and Nalbuphine Pivalate From Hydrogels by Passive Diffusions and Iontophoresis," Arzneimittelforschung, vol. 51, No. 5, pp. 408-413 (Abstract).
Fox S, et al. "Non-Subtype-Selective Opioid Receptor Antagonism in Treatment of Levodopa-Induced Motor Complications in Parkinson's Disease," Mov Disord, May 2004, vol. 19, No. 5, pp. 554-560 (Abstract).
Giuffra M., et al., "Dynorphin Agonist Therapy of Parkinson's Disease," Clin Neuropharmacol, Oct. 1993, vol. 16, No. 5, pp. 444-447 (Abstract).
Grunblatt E., et al., "Transcriptional Alterations Under Continuous or Pulsatile Dopaminergic Treatment in Dyskinetic Rats," J Neural Transm, Dec. 2011, vol. 118, No. 12, pp. 1717-1725, epub Dec. 25, 2010.
Han, RY, et al., "Mucoadhesive Buccal Disks for Novel Nalbuphine Prodrug Controlled Delivery: Effect of Formulation Variables on Drug Release and Mucoadhesive Performance," Int J Pharm, Jan. 1999, vol. 177, No. 2, pp. 201-209 (Abstract).
Henry B. et al., "Increased Striatal Pre-Proenkephalin B Expression is Associated with Dyskinesia in Parkinson's Disease," Exp Neurol, Oct. 2003, vol. 183, No. 2, pp. 458-468 (Abstract).
Henry B. et al., "Mu- and Delta-Opioid Receptor Antagonists Reduce Levodopa-Induced Dyskinesia in the MPTP-Lesioned Primate Model of Parkinson's Disease," Exp Neurol, Sep. 2001, vol. 171, No. 1, pp. 139-146 (Abstract).

Herrero MT, et al. "Effects of L-DOPA on Preproenkephalin and Preprotachykinin Gene Expression in the MPTP-Treated Monkey Striatum," Neuroscience, Oct. 1995, vol. 68, No. 4, pp. 1189-1198 (Abstract).
Huang, et al.,"The Effects of Electrically Assisted Methods on Transdermal Delivery of Nalbuphine Benzoate and Sebacoyl Dinalbuphine Ester From Solutions and Hydrogels," Int J Pharm, Jun. 2005, vol. 297, No. 1-2, pp. 162-171 (Abstract).
Ikeda K, et al. "TRK-820, a Selective Kappa Opioid Receptor Agonist, Could Effectively Ameliorate L-DOPA-Induced Dyskinesia Symptoms in a Rat Model of Parkinson's Disease," Eur J Pharmacol, Oct. 2009, vol. 620, No. 1-3, pp. 42-48 (Abstract).
Jenner P., "Molecular Mechanisms of L-DOPA-Induced Dyskinesia," Nat Rev Neurosci, Sep. 2008, vol. 9, No. 9, pp. 665-677 (Abstract).
Johansson PA, et al.,"Alterations in Cortical and Basal Ganglia Levels of Opioid Receptor Binding in a Rat Model of I-DOPA-Induced Dyskinesia," Neurobiol Dis, Apr. 2001, vol. 8, No. 2, pp. 220-239 (Abstract).
Klintenberg R., et al., "Naloxone Reduces Levodopa-Induced Dyskinesias and Apomorphine-Induced Rotations in Primate Models of Parkinsonism," J Neural Transm, Oct. 2002, vol. 109, No. 10, pp. 1295-1307 (Abstract).
Koprich JB, et al., "The Selective Mu-Opioid Receptor Antagonist ADL5510 Reduces Levodopa-Induced Dyskinesia Without Affecting Antiparkinsonian Action in MPTP-Lesioned Macaque Model of Parkinson's Disease," Mov Disord, Jun. 2011, vol. 26, No. 7, pp. 1225-1233, EPub Apr. 4, 2011 (Abstract).
Liu, Fl, et al."Biodegradable Polymeric Microspheres for Nalbuphine Prodrug Controlled Delivery: In Nitro Charactenzation and in Vivo Pharmacokinetic Studies," Int J Pharm, May 2003, vol. 257, No. 1-2, pp. 23-31 (Abstract).
Mansour A, et al. "Mu, Delta, and Kappa Opioid Receptor mRNA Expression in the Rat CNS: an In Situ Hybridization Study," J Comp Neurol, Dec. 1994, vol. 350, No. 3, pp. 412-438 (Abstract).
Mouradian MM, et al., "Pathogenesis of Dyskinesias in Parkinson's Disease," Ann Neurol, May 1989, vol. 25, No. 5, pp. 523-526 (Abstract).
Mouradian MM, et al., "Modification of Central Dopaminergic Mechanisms by Continuous Levodopa Therapy for Advanced Parkinson's Disease," Ann Neurol, Jan. 1990, vol. 27, No. 1, pp. 18-23 (Abstract).
Nisbet AP, et al.,"Preproenkephalin and Preprotachykinin Messenger RNA Expression in Normal Human Basal Ganglia and in Parkinson's Disease," Neuroscience, May 1995, vol. 66, No. 2, pp. 361-376 (Abstract).
Papa SM, et al., "Motor Fluctuations in Levodopa Treated Parkinsonian Rats: Relation to Lesion Extent and Treatment Duration," Brain Res, Oct. 1994, vol. 662, No. 1-2, pp. 69-74 (Abstract).
Papa SM and Chase TN, "Levodopa-Induced Dyskinesias Improved by a Glutamate Antagonist in Parkinsonian Monkeys," Ann Neurol, May 1996, vol. 39, No. 5, pp. 574-578 (Abstract).
Pao, LH, et al., "High-Performance Liquid Chromatographic Method for the Simultaneous Determination of Nalbuphine and Its Prodrug, Sebacoyl Dinalbuphine Ester, in Dog Plasma and Application to Pharmacokinetic Studies in Dogs," J Chromatogr B Biomed Sci Appl, Sep. 2000, vol. 746, No. 2, pp. 241-247 (Abstract).
Phillips, B., "Movement Disorders: A Sleep Specialist's Perspective," Neurology, Mar. 9, 2004, vol. 62, issue 5, supplement 2, pp. S9-S16 (Abstract).
Piccini P, et al., "Alterations in Opioid Receptor Binding in Parkinson's Disease Patients With Levodopa-Induced Dyskinesias," Ann Neurol, Nov. 1997, vol. 42, No. 5, pp. 720-726 (Abstract).
Potts, L.F, et al., "The Synthetic opioid nalbuphine reduces L-dopa-induced dyskinesia in non-human primates," The Movement Disorder Society MDS 17th International COngress of Parkinson's Disease and Movement Disorders, Sydney, Australia, vol. 28, Jun. 2013, pp. 1-2.
Rascol O, et al., "Naltrexone, an Opiate Antagonist, Fails to Modify Motor Symptoms in Patients With Parkinson's Disease," Mov Disord, Jul. 1994, vol. 9, No. 4, pp. 437-440 (Abstract).
Samadi P, et al., "Opioid Antagonists Increase the Dyskinetic Response to Dopaminergic Agents in Parkinsonian Monkeys: Inter- (56) References Cited

OTHER PUBLICATIONS action Between Dopamine and Opioid Systems," Neuropharmacology, Dec. 2003, vol. 45, No. 7, pp. 954-963 (Abstract).
Samadi P, et al., "The Opioid Agonist Morphine Decreases the Dyskinetic Response to Dopaminergic Agents in Parkinsonian Monkeys," Neurobiol Dis, Jun. 2004, vol. 16, No. 1, pp. 246-253 (Abstract).
Sandyk, R., et al., "Attenuation of reserpine-induced catalepsy by melatonin and the role of the opioid system," International J. of Neuroscience, Gordon and Breach, US, vol. 48, No. 3-4, Oct. 1989, pp. 297-301.
Sung, KC, et al. "Transdermal Delivery of Nalbuphine and Its Prodrugs by Electroporation," Eur J Pharm Sci, Jan. 2003, vol. 18, No. 1, pp. 63-70 (Abstract).
Sung, KC, et al., "Controlled Release of Nalbuphine Prodrugs From Biodegradable Polymeric Matrices: Influence of Prodrug Hydrophilicity and Polymer Composition," International Journal of Pharmaceutics, Apr. 1998, vol. 172, No. 1-2, pp. 17-25 (Abstract).
Verhagen ML, et al., "Amantadine as Treatment for Dyskinesias and Motor Fluctuations in Parkinson's Disease," Neurology, May 1998, vol. 50, No. 5, pp. 1323-1326 (Abstract).
Wang, JJ, et al. "Submicron Lipid Emulsion as a Drug Delivery System for Nalbuphine and Its Prodrugs," J Control Release, Oct. 2006, vol. 115, No. 2, pp. 140-149 (Abstract).
Westin JE, et al. "Spatiotemporal Pattern of Striatal ERK1/2 Phosphorylation in a Rat Model of L-DOPA-Induced Dyskinesia and the Role of Dopamine D1 Receptors," Biol Psychiatry, Oct. 2007, vol. 62, No. 7, pp. 800-810.

* cited by examiner

METHOD OF TREATING DYSKINESIA

CROSS-REFERENCE TO RELATED APPLICATIONS

The present application is a continuation-in-part of U.S. application Ser. No. 15/019,218, filed Feb. 9, 2016, which is a continuation-in-part of U.S. application Ser. No. 14/113,340, filed Mar. 6, 2014, the entire disclosure of which is hereby incorporated by reference, which is a national stage entry of PCT/US12/35129, filed Apr. 26, 2012, the entire disclosure of which is hereby incorporated by reference, which claims the benefit of priority under 35 U.S.C. § 119(e) of U.S. Provisional Application Ser. No. 61/480,415, filed on Apr. 29, 2011, the entire disclosure of which is incorporated herein by reference.

FIELD OF THE INVENTION

The present invention relates to a method of treatment for dyskinesias, including levodopa-induced dyskinesias (LID) in Parkinson's disease, and the dyskinesias associated with Tourette's syndrome, tardive dyskinesia and Huntington's disease.

BACKGROUND OF THE INVENTION

Parkinson's disease (PD) is the second most common neurodegenerative disorder afflicting 1.5 million individuals in the US and 6.3 million worldwide. The incidence of PD is expected to double by the year 2040. In the US, 50,000 new cases are diagnosed per year, and 1% of the population over the age of 55 is afflicted. The annual societal cost of PD is above $25 billion in the US alone.

The most common treatment for PD is 3,4-dihydroxyphenylalanine (levodopa or L-DOPA). While it remains the most effective therapy for the motor disability caused by PD, the vast majority of patients suffering from PD eventually develop a side effect characterized by abnormal involuntary movements known as L-DOPA induced dyskinesias (LID), which substantially compounds patient disability. Thus, LID is a common, devastating complication of the most efficacious therapeutic agent for PD. Dyskinesia is a disorder characterized by the presence of involuntary movements that are often uncontrollable. These movements are often choreiform (dance-like) in appearance but can also be more jerky and abrupt. They can affect any body parts including the arms and legs, muscles of the torso, chest, pelvis, face, lips, tongue, eyelids, and neck. It can even affect respiratory muscles. Some of these movements can be strong and violent that can lead to injuries including to the cervical spine (neck). Thus, dyskinesia is a major source of disability. Therefore, although L-DOPA is the gold standard in the management of PD, long-term treatment with L-DOPA is problematic. L-DOPA-induced dyskinesia affects 50% of treated PD patients by 5 years, and >90% by 10 years, which translates to an increase of approximately 10% per year. There are approximately 200,000 cases of LID in the US alone. Currently, amantadine (1-adamantanamine hydrochloride) is the only drug available that can modestly reduce LID, representing a deficient treatment with significant side effects of its own. Amantadine has an anti-dyskinetic effect likely due to its NMDA glutamate receptor antagonism, and it remains the only marketed agent with such a property. Several other experimental compounds targeting various transmitter systems have been tested, all with negative clinical trial outcomes. Moreover, in PD patients, LID is the main indication for the invasive and costly brain surgery known as Deep Brain Stimulation (DBS), an extreme option with the potential for serious neuropsychiatric side effects as well as the usual risks associated with invasive brain surgery. As a result, many patients are deemed poor candidates for this surgery, leaving their LID inadequately controlled.

Opioid receptors and LID

Central to the development of LID appear to be changes in neuronal networks that are modulated by glutamatergic, adenosinergic, adrenergic, dopaminergic, serotoninergic, endocannabinoid and opioid mediated neurotransmission, all of which have been characterized to be altered in disease. Of these, opioid receptor mediated neurotransmission is of particular interest as opioids are co-transmitters that modulate basal ganglia function. Through this action, opioid drugs may help blunt the negative effects of pulsatile stimulation with L-DOPA therapy that is pathogenically related to LID. In LID, precursors of endogenous opioid receptor ligands are massively upregulated, with preproenkephalin levels increased in the striatum in animal models, as well as being observed in postmortem studies of patients. Additionally, enkephalin, dynorphin and alpha-neoendorphin are elevated significantly in the dyskinetic state, but not in normal or nondyskinetic Parkinsonian state. Therefore, it has been proposed that opioid receptor antagonism may be of benefit. However, the complexity of the basal ganglia circuitry, the presence of opioid receptors both pre- and post-synaptically, and on both excitatory and inhibitory neurons, significantly compound the intricacies of the response to opioid receptor ligands that must be considered. There are three major relevant classes of opioid receptors with differential distributions in the basal ganglia and with different functions:

Delta ($\delta$)—Expressed predominantly in striatum and subthalamic nucleus, with lower levels in Globus Pallidus (GP) segments. These receptors regulate glutamate and acetylcholine release in the striatum.

Kappa ($\kappa$)—Expressed in all basal ganglia regions (striatum, GPe, GPi, STN, SN) & thalamus.

Mu ($\mu$)—Expressed in all basal ganglia regions and thalamus.

Further complexity arises as expression of opioid receptors change in the Parkinsonian state. For example, kappa receptors are decreased in substantia nigra, and kappa and mu receptors are decreased in GPi in LID, likely secondary to alterations in opioid ligand expression. This complexity in distribution and function is probably the reason why nonselective antagonists have shown extremely varied efficacy in LID, worsening, not affecting, or ameliorating symptoms in animal models, and have not been effective in small clinical trials. Therefore, a level of specificity is believed to be required, but the precise nature of this specificity appears to be complex. The effects of more compounds can be summarized as follows:

- The $\mu$-opioid receptor selective antagonist cyprodime significantly reduces peak-dose LID. However, the selective p-opioid receptor antagonist ADL5510 reduces LID but with a U-shaped dose response curve
- The $\kappa$-opioid receptor selective agonist U50,488 reduces LID but worsens parkinsonism in MPTP-treated primates. However, the $\kappa$-opioid receptor selective antagonist nor-BNI moderates levodopa-induced hyperkinesias in the 6-hydroxydopamine-lesioned rat model.
- Lower doses of the selective $\delta$-opioid receptor antagonist naltrindole reduce levodopa-induced rotations in hemiparkinsonian marmoset monkeys.

Morphine (nonselective opioid receptor agonist) reduces dyskinetic movements in Parkinsonian primates and patients Naloxone and Naltrexone (nonselective opioid receptor antagonists) have been tested with variable effects in monkeys and humans reporting no change, increases or decreases in LID.

Collectively, the compounds tested to date indicate potential for modulating opioid receptors, but also indicate great complexity. Even those that are efficacious at some doses may display U-shaped dose response curves as non-specificity becomes an issue such as occurs with ADL5510. Consideration of these studies indicates that the most efficacious anti-dyskinetic agent acting on the opioid receptor system would have an as yet undiscovered mixture of pharmacological actions on different opioid receptors.

Safety Considerations of Opioid Drugs

Activation of opioid receptors is achieved by a number of widely used and abused opiates such as morphine and codeine. Despite the clear beneficial effects that these compounds can have in analgesia and other indications, they can have severe addictive and sedative effects, while antagonists can precipitate withdrawal symptoms in patients on opiates. Therefore, doses relevant for LID need to be considered in light of these side effects. The major specific side effects relevant to mu-antagonists are related to the gastrointestinal tract and dysphoria, while for kappa-agonists are sedation, worsening parkinsonism and dysphoria for example.

In summary, in LID there are increases in the release of opioid peptide precursors, therefore, modulation of opioid receptors is an attractive therapeutic approach. The complexity of how different opioid receptors regulate signaling at different sites within the circuitry of the basal ganglia dictates the selectivity profile that will be efficacious to modulate. The broad spectrum opioid receptor antagonists, such as Naloxone and Naltrexone, have been proposed as possible therapeutics, but have not been clinically successful. Selective agents for specific opioid receptor isoforms may offer limited benefits, but also demonstrate opposing dose-dependent effects that can substantially reduce their utility with significant dose-limiting adverse effects.

Thus, there remains a significant need for a therapeutic agent to treat L-DOPA-induced dyskinesias, since LID is a critical condition affecting a large and increasing population of PD patients. Further, there are other orphan diseases that exhibit dyskinesias for which treatments are unavailable or inadequate; these diseases include Huntington's disease, Tourette's syndrome and tardive dyskinesia. The present invention addresses these unmet needs.

BRIEF SUMMARY OF THE INVENTION

The present invention relates to a novel use of dual-action μ-opioid receptor antagonist/κ-opioid receptor agonists as therapeutic agents to treat dyskinesias, especially L-DOPA induced dyskinesias (LID), common in PD patients.

In some embodiments of the invention, the dual-action μ-opioid receptor antagonist/κ-opioid receptor agonists include but are not limited to such agents as Nalbuphine, Butorphanol, Pentazocine, Nalorphine, Naltriben, Alazocine, Atomoxetine, Bremazocine, Salvinorin A, Samidorphan, Nalmefene, Nalodeine, related compounds and the prodrugs thereof.

In some embodiments, the invention comprises treatment of dyskinesias, including but not limited to LID, tardive dyskinesias, Huntington's chorea, and Tourette's syndrome with Nalbuphine. In further, the present invention comprises the use of dual-action μ-opioid receptor antagonist/κ-opioid receptor agonists in the treatment of LID.

In some embodiments, the dual-action μ-opioid receptor antagonist/κ-opioid receptor agonist is Nalbuphine or prodrugs thereof:

In some embodiments, the dual-action μ-opioid receptor antagonist/κopioid receptor agonist comprises Butorphanol or prodrugs thereof:

In some embodiments, dual-action μ-opioid receptor antagonist/κ-opioid receptor agonist comprises Pentazocine or prodrugs thereof:

Pentazocine

In some embodiments, the dual-action μ-opioid receptor antagonist/κ-opioid receptor agonist comprises Nalorphine or prodrugs thereof:

Nalorphine

In some embodiments, the dual-action μ-opioid receptor antagonist/κ-opioid receptor agonist comprises Naltriben or prodrugs thereof:

Naltriben

In some embodiments, the dual-action μ-opioid receptor antagonist/κ-opioid receptor agonist comprises Alazocine or prodrug thereof:

Alazocine

In some embodiments, the dual-action μ-opioid receptor antagonist/κ-opioid receptor agonist comprises Atomoxetine, or prodrug thereof:

Atomoxetine

In some embodiments, the dual-action μ-opioid receptor antagonist/κ-opioid receptor agonist comprises Bremazocine, or prodrug thereof:

Bremazocine

In some embodiments, the dual-action μ-opioid receptor antagonist/κ-opioid receptor agonist comprises Salvinorin A, or prodrug thereof:

Salvinorin A

In some embodiments, the dual-action μ-opioid receptor antagonist/κ-opioid receptor agonist comprises Samidorphan, or prodrug thereof:

Samidorphan

In some embodiments, the dual-action μ-opioid receptor antagonist/κ-opioid receptor agonist comprises Nalmefene or prodrugs thereof:

Nalmefene

In some embodiments, the dual-action μ-opioid receptor antagonist/κ-opioid receptor agonist comprises Nalodeine or prodrug thereof:

Nalodeine

In one embodiment, the present invention relates to methods of treating or mitigating various forms of dyskinesia, including, but not limited to, LID, especially in PD patients; tardive dyskinesias; Tourette's syndrome; and Huntington's disease, comprising administering a therapeutically effective amount of a dual-action μ-opioid receptor antagonist/κ-opioid receptor agonist to a patient in need thereof sufficient to mitigate the dyskinesia. Mitigation of dyskinesia is defined as reduced severity and/or duration of abnormal involuntary movements based on validated scales administrated by trained personnel and, specifically for LID, by patient diaries marking "on with non-troublesome dyskinesia" or "on with troublesome dyskinesia." Treating includes post diagnosis and prophylactic treatment of patients suffering from LID; tardive dyskinesias; Tourette's syndrome; and Huntington's disease, or are at risk of developing such conditions.

The dual-action μ-opioid receptor antagonist/κ-opioid receptor agonist can be selected from Nalbuphine, Nalorphine, Pentazocine, Butorphanol, Naltriben, Alazocine, Atomoxetine, Bremazocine, Salvinorin A, Samidorphan, Nalmefene, Nalodeine, and combinations of two or more thereof, their prodrugs or related compounds. Preferably, but not necessarily, the dual-action μ-opioid receptor antagonist/κ-opioid receptor agonist comprises Nalbuphine.

Another embodiment of the invention comprises administering a therapeutically effective amount of a dual-action μ-opioid receptor antagonist/κ-opioid receptor agonist to a subject in need thereof in a non-injectable composition comprising:
 a. said dual-action μ-opioid receptor antagonist/κ-opioid receptor agonist in the form of a free-base or a pharmaceutically acceptable derivative, prodrug or salt, in an amount of at least 0.01 milligram; and
 b. a pharmaceutically acceptable carrier;
where the composition is in tablet or capsule form. Preferably the dual-action μ-opioid receptor antagonist/κ-opioid receptor agonist composition is administered orally. Preferably component a. is present in an amount of at least 0.1 mg. In some embodiments, the dual-action μ-opioid receptor antagonist/κ-opioid receptor agonist is selected from Nalbuphine, Nalorphine, Pentazocine, Butrophanol, Naltriben, Alazocine, Atomoxetine, Bremazocine, Salvinorin A, Samidorphan, Nalmefene, Nalodeine, and combination of two or more thereof, their prodrugs, or related compounds. Preferably, but not necessarily, the dual-action μ-opioid receptor antagonist/κ-opioid receptor agonist comprises Nalbuphine.

In yet another embodiment of the invention, the dual-action mu-antagonist/kappa-agonist comprises a dual-action μ-opioid receptor antagonist/κ-opioid receptor agonist administered to a subject via a continuous infusion or non-continuous intermittent infusion. In some embodiments, the dual-action μ-opioid receptor antagonist/κ-opioid receptor agonist is selected from Nalbuphine, Nalorphine, Pentazocine, Butrophanol, Naltriben, Alazocine, Atomoxetine, Bremazocine, Salvinorin A, Samidorphan, Nalmefene, Nalodeine, and combination of two or more thereof, their prodrugs, or related compounds. Preferably, but not necessarily, the dual-action μ-opioid receptor antagonist/κ-opioid receptor agonist comprises Nalbuphine. Preferably the continuous infusion dose is at least about 0.0001 mg/kg/day.

Another embodiment of the invention is directed to a method of treatment including prophylactic treatment as well as post diagnosis treatment to mitigate dyskinesia comprising administering therapeutically effective amounts of both a mu (μ)-opioid receptor antagonist and a kappa (κ)-opioid receptor agonist to a subject in need thereof, sufficient to mitigate said dyskinesia. The agents may be administered together or separately. In at least one embodiment, the therapeutic agents of the present invention are able to provide antagonistic interaction at the μ-opioid receptor while also able to provide an agonistic activity once bound to the κ-opioid receptor at the desired site. In another embodiment, the antagonistic interaction at the μ-opioid receptor may be provided by a different active ingredient than the one that provides the agonistic activity at the κ-opioid site.

Prophylactic treatment comprises administering the effective amount of an antagonist of μ-opioid receptor and an agonist of the κ-opioid receptor to a subject at risk of developing LID, tardive dyskinesia, Tourette's syndrome, or Huntington's disease. Such subject for example may include patients who are candidates for l-dopa therapy, antipsychotic therapy, or have such risk factors that are recognized by those of ordinary skill in the art to be associated with risk of developing dyskinesia, Tourette's syndrome, or Huntington's disease associated signs and symptoms. Patients who are candidates for such prophylactic therapy include Parkinson's disease patients treated with L-dopa and are therefore at risk of developing L-dopa induced dyskinesia, psychiatric patients treated with anti-psychotic agents at risk of developing tardive dyskinesia, and chorea of the Huntington's disease gene at risk of developing chorea.

In yet another embodiment, the antagonistic interaction at the μ-opioid receptor and the agonistic activity to the κ-opioid receptor may occur simultaneously. In yet another embodiment the antagonistic interaction at the μ-opioid receptor and the agonistic activity to the κ-opioid receptor overlap temporally with the duration of one activity extending beyond the other. In yet another embodiment, the temporal overlap may be provided by pharmacologically active agents that possess an IC50 for μ-opioid receptors of about 4200, an IC50 for κ-opioid receptors of about 4383 nM, and a IC50 for δ-opioid receptors of about >5000 nM.

In yet another embodiment, the therapeutic agents of the present invention may have a $K_i$ for μ-opioid receptors of about ranging from 0.1 nm to about 2600 nM, a $K_i$ for κ-opioid receptors of about 0.050 to 10 nM, and a $K_i$ for δ-opioid receptors of about >1000 nM.

In a preferred embodiment, the $K_i$ for μ-opioid receptors is from about 0.1 nM to about 100 nM and a Ki for κ-opioid receptors from about 0.1 nM to about 100 nM.

A further embodiment of the invention is directed to a method of treating or mitigating a dyskinesia, comprising administering a therapeutically effective amount of a prodrug of a dual-action mu-opioid receptor antagonist/kappa-opioid receptor agonist to a subject in need thereof, sufficient to mitigate said dyskinesia. Preferably, the prodrug is a prodrug of Nalbuphine, most preferably an ester of Nalbuphine, optionally as a pharmaceutically acceptable salt.

In some embodiments of this invention, the μ-opioid receptor antagonist/κ-opioid receptor agonist has a $K_i$ for μ-opioid receptors from about 0.1 nM to about 100 nM and a $K_i$ for δ-opioid receptors of about 10-100, and a Ki for κ-opioid receptors from about 0.1 nM to about 10 nM.

In some embodiments of this invention, the dual-action μ-opioid receptor antagonist/κ-opioid receptor agonist has a $K_i$ for μ-opioid receptors from about 0.22 nM to about 69 nM and a $K_i$ for κ-opioid receptors from about 0.12 nM to about 29 nM.

In some embodiments of this invention, the dual-action μ-opioid receptor antagonist/κ-opioid receptor agonist has a $K_i$ for μ-opioid receptors of about 0.22 nM and a $K_i$ for κ-opioid receptors of about 0.12 nM.

In some embodiments of this invention, the dual-action μ-opioid receptor antagonist/κ-opioid receptor agonist has a $K_i$ for μ-opioid receptors of about 0.5 nM and a $K_i$ for κ-opioid receptors of about 29 nM.

In some embodiments of this invention, the dual-action μ-opioid receptor antagonist/κ-opioid receptor agonist has a $K_i$ for μ-opioid receptors of about 69 nM and a $K_i$ for κ-opioid receptors of about 2.2 nM.

In some embodiments of this invention, the dual-action μ-opioid receptor antagonist/κ-opioid receptor agonist has a $K_i$ for μ-opioid receptors of about 8.13 nM and a $K_i$ for κ-opioid receptors of about 7.66 nM.

DETAILED DESCRIPTION OF PREFERRED EMBODIMENTS

Dual-Action μ-Opioid Receptor Antagonist/κ-Opioid Receptor Agonists

The following compounds, Nalbuphine, Butorphanol, Pentazocine, Nalorphine, Naltriben, Alazocine, Atomoxetine, Bremazocine, Salvinorin A, Samidorphan, Nalmefene, and Nalodeine have properties required to be an effective agent for the treatment of dyskinesias, including LID, tardive dyskinesia, Huntington's chorea, and Tourette's Syndrome, with a safety window that makes their use viable at sub-analgesic, non-sedative doses. These compounds exhibit activity as dual-action μ-opioid receptor antagonist/κ-opioid receptor agonists. As such, they provide the opportunity to combine these two activities into a single, safe, therapeutic agent. Thus, dual-action μ-opioid receptor antagonist/κ-opioid receptor agonists offer key pharmacological advantages such as fixed ratio of μ-antagonism/κ-agonism in relevant brain compartments, regardless of dose, dosage form or stage of the disease in a particular patient. These dual-action μ-opioid receptor antagonist/κ-opioid receptor agonists, including Nalbuphine, Butorphanol, Pentazocine and Nalorphine display a linear dose-response curve, as opposed to a U-shaped dose response curve that is characteristic of many μ-antagonists and κ-agonists. This linear dose-response curve results in several distinct medical advantages. First, the linear dose-response curve allows for much more predictable dosage at sub-analgesic levels. Second, this unique characteristic results in the ability to treat dyskinesias without risk of exposing a patient to excessive kappa agonism which has been reported to cause adverse effects, such as behavioral changes in Parkinson patients and other disease states, and respiratory depression.

TABLE 1

Selectivity of dual-action μ-opioid receptor antagonist/κ-opioid receptor agonists
Dual-Action μ-Opioid Receptor Antagonist/κ-Opioid Receptor Agonists

| | Opioid Receptor Types | |
|---|---|---|
| Opioid Ligands | Mu (μ) (MOR) | Kappa (κ) (KOR) |
| Pentazocine | – | ++ |
| Nalbuphine | --- | ++ |
| Butorphanol | +/– | ++ |
| Nalorphine | – | ++ |

In certain embodiments, the dual-action μ-opioid receptor antagonist/κ-opioid receptor agonists may possess an IC50 for μ-opioid receptors of about 4200, an IC50 for κ-opioid receptors of about 4383 nM, and a IC50 for δ-opioid receptors of about >5000 nM. In other embodiments, the dual action opioid receptor modulator of the present invention may have a $K_i$ for μ-opioid receptors of about ranging from 0.1 nm to about 2600 nM, a $K_i$ for κ-opioid receptors of about 0.050 to 10 nM, and a $K_i$ for δ-opioid receptors of about >1000 nM. In a preferred embodiment, the $K_i$ for μ-opioid receptors is from about 0.1 nM to about 100 nM and a Ki for κ-opioid receptors from about 0.1 nM to about 100 nM.

Nalbuphine

Nalbuphine (Nubain) is a synthetic opioid with activity as both a mu-opioid receptor antagonist and a kappa-opioid receptor agonist. It has been used clinically since 1979 as an analgesic for moderate/severe pain including for women in labor. It is the only narcotic of its type that is not regulated under the Controlled Substances Act, an indication of its safety, with the major side effect being mild sedation at analgesic doses in a subset of people. Nalbuphine exhibits a Ki for μ-receptors about 0.5 nM, a Ki for κ-receptors about 29 nM, and for δ-receptors about 60 nM. Another surprising finding is that kappa agonism of Nalbuphine exerts its anti-LID efficacy without worsening Parkinsonism.

Nalbuphine functions by modulating locomotion by interacting with μ-opioid receptors as an antagonist and κ-opioid receptors as an agonist. Nalbuphine administration offers a distinct advantage in that it does not cause significant euphoric, dysphoric or sedative effects, at the doses of the present invention. Additionally, the method of the present invention does not impair cognition or respiration. Furthermore, Nalbuphine has been shown to be safe (in 30 years of clinical use as an analgesic), non-addictive at sub-analgesic doses, and having a "ceiling effect" that limits adverse effects at higher doses.

Currently, Nalbuphine is administered for pain relief as an intramuscular injection, which is not necessarily a desirable route for chronic administration in LID or other chronic conditions. Due to its safety and efficacy, oral forms may be preferable. Oral formulations of Nalbuphine are disclosed in the following patents or patent publications: U.S. Pat. No. 6,703,398; US 2009/0030026; EP 2402005; WO 2007/127683 and US 2009/0060871 incorporated herein by reference. Although these have been proven efficacious, they are not commercially viable in the field of analgesia and, thus, their further development and marketing has not been achieved. This invention indicates proof-of-concept data with the injectable dosage form in the primate model of PD with LID.

Butorphanol

Butorphanol is a synthetic morphinan analgesic that exhibits activity as a dual-action μ-opioid receptor antagonist/κ-opioid receptor agonist. Butorphanol has a $K_i$ for μ-opioid receptors of about 0.22 nM, a $K_i$ for κ-opioid receptors of about 0.12 nM, and a $K_i$ for δ-opioid receptors of about 12 nM.

Pentazocine

Pentazocine is a synthetically-prepared drug of the benzomorphan class of opioids that exhibits activity as a dual-action μ-opioid receptor antagonist/κ-opioid receptor agonist. Pentazocine was first approved by the FDA for use in 1967. Pentazocine has a $K_i$ for μ-opioid receptors of about 69 nM, and a $K_i$ for κ-opioid receptors of about 2.2 nM.

Nalorphine

Nalorphine (N-allyl-normorphine) exhibits activity as a dual-action μ-opioid receptor antagonist/κ-opioid receptor agonist. Nalorphine has a $K_i$ for μ-opioid receptors of about 8.13 nM, a $K_i$ for κ-opioid receptors of about 7.66 nM, and a $K_i$ for δ-opioid receptors of about 6.33 nM.

Naltriben

Naltriben exhibits activity as a dual-action μ-opioid receptor antagonist/κ-opioid receptor agonist. Naltriben has a $K_i$ for μ-opioid receptors of about 19.79±1.12 nM, a $K_i$ for κ-opioid receptors of about 82.75±6.32 nM, and a $K_i$ for δ-opioid receptors of about 0.28±0.11 nM.

Alazocine

Alazocine exhibits activity as a dual-action μ-opioid receptor antagonist/κ-opioid receptor agonist. Alazocine has a $K_i$ for μ-opioid receptors of about 3.0 nM, a $K_i$ for κ-opioid receptors of about 4.7 nM, and a $K_i$ for δ-opioid receptors of about 15 nM.

Atomoxetine

Atomoxetine exhibits activity as a dual-action μ-opioid receptor antagonist/κ-opioid receptor agonist. Atomoxetine has a IC50 for μ-opioid receptors of about 4186 nM, a IC50 for κ-opioid receptors of about 4383 nM, and a IC50 for δ-opioid receptors of less than 5000 nM.

Bremazocine

Bremazocine exhibits activity as a dual-action μ-opioid receptor antagonist/κ-opioid receptor agonist. Bremazocine has a $K_i$ for μ-opioid receptors of about 1.6 nM, a IC50 for κ-opioid receptors of about 0.16±0.05 nM, and a $K_i$ for δ-opioid receptors of less than 1000 nM nM.

Salvinorin A

Salvinorin A exhibits activity as a dual-action μ-opioid receptor antagonist/κ-opioid receptor agonist. Salvinorin A has a $K_i$ for μ-opioid receptors of about 2549 nM, a $K_i$ for κ-opioid receptors of about 6.2±2.2 nM, and a $K_i$ for δ-opioid receptors of less than 1000 nM.

Samidorphan

Samidorphan exhibits activity as a dual-action μ-opioid receptor antagonist/κ-opioid receptor agonist. Samidorphan has a $K_i$ for μ-opioid receptors of about 0.052 nM, a $K_i$ for κ-opioid receptors of about 0.23 nM, and a $K_i$ for δ-opioid receptors of about 2.6 nM.

Nalmefene

Nalmefene exhibits activity as a dual-action μ-opioid receptor antagonist/κ-opioid receptor agonist. Nalmefene has a $K_i$ for μ-opioid receptors of about 0.24 nM, a $K_i$ for κ-opioid receptors of about 0.083 nM, and a $K_i$ for δ-opioid receptors of about 16 nM.

Nalodeine

Nalodeine exhibits activity as a dual-action μ-opioid receptor antagonist/κ-opioid receptor agonist. Nalodeine has a $K_i$ for μ-opioid receptors of about 0.1 nM to about 100 nM and a Ki for κ-opioid receptors from about 0.1 nM to about 100 nM and $K_i$ for δ-opioid receptors of less than 1000 nM.

Dyskinesia

Hyperkinetic movement disorders exhibit considerable similarities both phenomenologically and pharmacologically. Thus, L-DOPA induced dyskinesia (LID), chorea of Huntington's Disease, neuroleptic-induced tardive dyskinesia, and Tourette's Syndrome all exhibit excessive involuntary movements, as does L-dopa induced dyskinesia (LID) in Parkinson patients, and are all suppressed by anti-dopaminergic agents. Additionally, modulation of opiate transmission can impact the abnormal involuntary movements in these conditions.

Accordingly, one particular embodiment of the present invention is directed to the use of a dual-action μ-opioid receptor antagonist/κ-opioid receptor agonist agent, represented by Nalbuphine and related compounds, including Butorphanol, Pentazocine, Nalorphine, Naltriben, Alazocine, Atomoxetine, Bremazocine, Salvinorin A, Samidorphan, Nalmefene, and Nalodeine in the treatment of LID and dyskinesias associated with other diseases such as tardive dyskinesias, Tourette's syndrome and Huntington's disease. Further, the invention is also directed to the treatment of such dyskinesias with a combination of both a μ-opioid receptor antagonist and a κ-opioid receptor agonist. This combination of drugs may be administered together or separately. If administered separately, various time delays between the administration of the individual dosage forms are possible, depending on the needs of the patient. If administered together, a combination of individual dosage forms may be given, or the drugs may be formulated as a single composition.

L-DOPA Induced Dyskinesia (LID)

One embodiment of the present invention relates to the novel use of dual-action μ-opioid receptor antagonist/κ-opioid receptor agonist, represented by Nalbuphine and related compounds including Butorphanol, Pentazocine, Nalorphine, Naltriben, Alazocine, Atomoxetine, Bremazocine, Salvinorin A, Samidorphan, Nalmefene, and Nalodeine, or prodrugs thereof as a therapeutic agent to treat L-DOPA induced dyskinesias (LID) common in PD patients. It is known that opioid transmission in the basal ganglia is an integral part of voluntary movement control; thus, this mechanism has been implicated in LID. Although modulation of specific opioid receptors has been proposed as a treatment for LID, the experimental agents examined to date have resulted in clinical inefficacy and unacceptable side effects.

Tardive Dyskinesia

One embodiment of the present invention relates to the novel use of dual-action μ-opioid receptor antagonist/κ-opioid receptor agonist, represented by Nalbuphine and related compounds including Butorphanol, Pentazocine, Nalorphine, Naltriben, Alazocine, Atomoxetine, Bremazocine, Salvinorin A, Samidorphan, Nalmefene, Nalodeine, or prodrugs thereof as a therapeutic agent to treat tardive dyskinesia. Without wishing to be bound by theory, tardive dyskinesia is believed to result from nigrostriatal dopaminergic supersensitivity secondary to prolonged neuroleptic (dopamine receptor antagonist) exposure, which occurs in 20-30% of patients treated with neuroleptics. While the exact pathogenesis of tardive dyskinesia remains elusive, altered opioid peptide function in striatal projection pathways of the basal ganglia has been implicated.

Huntington's Chorea

One embodiment of the present invention relates to the novel use of dual-action μ-opioid receptor antagonist/κ-opioid receptor agonist, represented by Nalbuphine and related compounds including Butorphanol, Pentazocine, Nalorphine, Naltriben, Alazocine, Atomoxetine, Bremazocine, Salvinorin A, Samidorphan, Nalmefene, Nalodeine, or prodrugs thereof as a therapeutic agent to treat Huntington's Chorea. Without wishing to be bound by theory, the chorea of Huntington's disease is believed to be due to excessive dopaminergic tone in the basal ganglia and is therefore treated with agents that deplete dopamine (tetrabenazine, the only FDA approved treatment for chorea in HD) or block dopamine receptors (neuroleptics such as haloperidol, olanzapine and aripiprazole). These agents that counter the effects of dopamine also diminish LID in Parkinson patients, but because anti-dopaminergic drugs worsen parkinsonism they are contraindicated in Parkinson disease. Also, similar to LID, the NMDA antagonist amantadine reduces chorea in Huntington's disease patients. In Huntington's disease, which is characterized by degeneration of striatal neurons, endogenous opiates are decreased in the brain and in the cerebrospinal fluid. Accordingly, striatal pre-enkephalin overexpression improves Huntington's disease symptoms in the R6/2 mouse model of the disease.

Tourette's Syndrome

One embodiment of the present invention relates to the novel use of dual-action μ-opioid receptor antagonist/κ-opioid receptor agonist, represented by Nalbuphine and related compounds including Butorphanol, Pentazocine, Nalorphine, Naltriben, Alazocine, Atomoxetine, Bremazocine, Salvinorin A, Samidorphan, Nalmefene, Nalodeine or prodrugs thereof as a therapeutic agent to treat Tourette's Syndrome. In Tourette's Syndrome, opiate receptors are reported as abnormal.

Treatment Methods

One embodiment of the present invention offers a novel method of treatment of LID and other dyskinesias using such dual-action μ-opioid receptor antagonist/κ-opioid receptor agonist agents, which have the advantages of possessing a low incidence of side effects, a "ceiling" for side effects, and being non-addictive. Furthermore, such dual-acting therapeutic agents, including Nalbuphine, Butorphanol, Pentazocine, Nalorphine, Naltriben, Alazocine, Atomoxetine, Bremazocine, Salvinorin A, Samidorphan, Nalmefene, and Nalodeine have surprisingly increased efficacy compared to other strategies and address an area of medicine with major, unmet needs, vide infra.

In another embodiment, the present invention provides for prophylactic treatments of patients at risk of developing L-dopa induced dyskinesia, tardive dyskinesia, Tourette's syndrome, or Huntington's disease comprising administering effective amounts of an antagonist of μ-opioid receptor and an agonist to the κ-opioid receptor to a subject in need of such treatment. For example, a subject may prophylactically be treated with the compositions of the present invention before or during his or her course of levodopa therapy.

In yet another embodiment, the antagonistic interaction at the μ-opioid receptor and the agonistic activity to the κ-opioid receptor may occur simultaneously. In yet another embodiment the antagonistic interaction at the μ-opioid receptor and the agonistic activity to the κ-opioid receptor overlap temporally with the duration of one activity extending beyond the other. In yet another embodiment, pharmacologically active agents employed in the presently described invention possess a Ki for μ-opioid receptors from about 0.1 nM to about 100 nM and/or a Ki for κ-opioid receptors from about 0.1 nM to about 100 nM.

In another embodiment, the present invention is directed to a method of treating or mitigating various types of dyskinesia, including, but not limited to, LID, especially in PD patients; tardive dyskinesias; Tourette's syndrome; and Huntington's disease and related diseases, comprising administering a composition comprising both a μ-opioid receptor antagonist and a κ-opioid receptor agonist.

In another embodiment, the present invention is directed to a method of treating or mitigating various types of dyskinesias, including, but not limited to LID, especially in PD patients; tardive dyskinesias; Tourette's syndrome; and Huntington's disease and related diseases, comprising administering a composition comprising a single therapeutic agent which is active both as a mu-opioid receptor antagonist and a kappa-opioid receptor agonist. Representative of such dual-action μ-opioid receptor antagonist/κ-opioid receptor agonist agents is the synthetic analgesic opioid, Nalbuphine, as well as Butorphanol, Pentazocine, Nalorphine, Naltriben, Alazocine, Atomoxetine, Bremazocine, Salvinorin A, Samidorphan, Nalmefene, and Nalodeine.

In another embodiment, the present invention is directed to a method of treating or mitigating dyskinesias comprising administering Nalbuphine, Nalorphine, Pentazocine, Butorphanol, Naltriben, Alazocine, Atomoxetine, Bremazocine, Salvinorin A, Samidorphan, Nalmefene, and Nalodeine or a combination of two or more of these, or their prodrugs. In yet another embodiment, the compositions of the present invention may further include an additional μ-opioid receptor antagonist or κ-opioid receptor agonist.

In a more specific embodiment, the present invention is directed to a method of treating or mitigating various types of dyskinesias in a patient in need thereof, including, but not limited to LID, especially in PD patients; tardive dyskinesias; Tourette's syndrome; and Huntington's disease, comprising administering a safe and effective amount of a dual-action μ-opioid receptor antagonist/κ-opioid receptor agonist, including but not limited to Nalbuphine, Butorphanol, Pentazocine, Nalorphine, Naltriben, Alazocine, Atomoxetine, Bremazocine, Salvinorin A, Samidorphan, Nalmefene, and Nalodeine, preferably in the dosage range of about 0.001 mg/kg to about 3 mg/kg.

In another embodiment, the present invention is directed to a method of treating or mitigating dyskinesias comprising administering to a subject in need thereof a non-injectable or injectable pharmaceutical composition comprising a combination of both a μ-opioid receptor antagonist and a κ-opioid receptor agonist, or alternatively, comprising a dual-action μ-opioid receptor antagonist/κ-opioid receptor agonist possessing both μ-opioid receptor antagonist and κ-opioid receptor agonist activities, including Nalbuphine, Butorphanol, Pentazocine Nalorphine, Naltriben, Alazocine, Atomoxetine, Bremazocine, Salvinorin A, Samidorphan, Nalmefene, Nalodeine in various administration vehicles, including but not limited to tablets, capsules, caplets, syrups, gels, suppositories, inhalable powders, inhalable aerosols, sublingual sprays, sublingual solid dosage form, patch, intranasal sprays, intranasal aerosols, injectable solutions and injectable suspensions including those delivered via minipumps and other devises capable of continuous delivery of the agent. If the pharmaceutical composition is administered by injection, the injection may be intravenous, subcutaneous, intramuscular, intraperitoneal or by other means known in the art. The present invention may be formulated by any means known in the art, including but not limited to formulation as suspensions, powders, lyophilized preparations, ocular drops, skin patches, oral soluble formulations, sprays, aerosols and the like, and may be mixed and formulated with buffers, binders, excipients, stabilizers, antioxidants and other agents known in the art. Administration means may include administration through mucous membranes, buccal administration, oral administration, dermal administration, inhalation administration, nasal administration, troches, lozanges and the like.

In another embodiment, the present invention is directed to methods of orally administering a controlled-release dosage forms comprising a dual-action μ-opioid receptor antagonist and κ-opioid receptor agonist. Such dosage form may include a controlled release material which is incorporated into a matrix along with the dual μ-opioid receptor antagonist and κ-opioid receptor agonist. In yet another embodiment, the controlled release material is applied as a sustained release coating over a bead, pellet, spheroid or a tablet core comprising a dual-action μ-opioid receptor antagonist/κ-opioid receptor agonist possessing both μ-opioid receptor antagonist and κ-opioid receptor agonist activity. The controlled release material may be hydrophobic or hydrophilic as desired.

In yet another embodiment, the oral dosage form according to the invention may be provided as, for example, granules, spheroids, pellets or other multiparticulate formulations. An effective amount of such granules, pellets or multiparticulate containing the desired μ-opioid receptor antagonistic and κ-opioid receptor agonistic amounts may be placed in a capsule or may be incorporated in any other suitable oral solid form, e.g., compressed into a tablet. Optionally other pharmaceutically desirable ingredients (e.g., diluents, binders, colorants, lubricants, etc.) may be used to achieve the desired pharmacokinetics and pharmacodynamics properties.

In yet another embodiment, the controlled-release dosage forms may include a μ-opioid receptor antagonist and a κ-opioid receptor agonist in such ratios providing a $K_i$ for μ-opioid receptors from about 0.1 nM to about 100 nM and a Ki for κ-opioid receptors from about 0.1 nM to about 100 nM. In a more preferred embodiment, the controlled-release dosage forms include a μ-opioid receptor antagonist as well as a κ-opioid receptor agonist possessing a $K_i$ for μ-opioid receptors from about 0.22 nM to about 69 nM and a $K_i$ for κ-opioid receptors from about 0.12 nM to about 29 nM.

In a preferred embodiment, the present invention is directed to a method of treating or mitigating dyskinesias, including LID, tardive dyskinesia, Huntington's chorea, and Tourette's Syndrome, comprising administering to a subject in need thereof a non-injectable, pharmaceutically acceptable oral formulation comprising an active component including free-base Nalbuphine or a pharmaceutically acceptable derivative or salt of Nalbuphine, and a pharmaceutically acceptable carrier or adjuvant; and wherein the formulation is in tablet or capsule form. For the present invention, the term "derivative" means a compound derived from a drug molecule, for example Nalbuphine, which can regenerate or release the parent drug (e.g, Nalbuphine) at a target site in vivo, for example when acted upon by hydrolytic and/or oxidative enzymes. Such derivatives are known as "prodrugs" in the medicinal chemistry arts. Prodrugs are generally derivatives of the drug, for example esters of carboxylic acids, or conjugates with amino acids, peptides or proteins. Prodrug derivatives influence the uptake, transport, toxicity and/or metabolism properties of the parent drug.

There are known Nalbuphine prodrugs designed to improve its pharmacokinetic and pharmacodynamic profiles. For example, Nalbuphine can be modified at the phenolic hydroxyl by acylation to form esters or by alkylation to form ethers. Furthermore, Nalbuphine can be coupled to an amino acid or short peptide. Also, Nalbuphine can be modified with dicarboxylic acids themselves or dicarboxylic acid linked-amino acids or dicarboxylic acid linked-peptides. Further, Nalbuphine can be modified with a carbamate-linked amino acid or peptide. Nalbuphine can be further modified on its nitrogen atom by forming salts or N-oxides. As discussed above, Nalbuphine can be converted to ester prodrugs which increase its bioavailability. More specifically, formulation to increase Nalbuphine's bioavailability can include vegetable oils, a co-solvent, and an effective amount of a Nalbuphine ester prodrug or a pharmaceutically acceptable salt thereof, which can increase the oral bioavailability of Nalbuphine by more than 12 times, and prolong the retention time of Nalbuphine in the body, thereby maintaining a longer analgesic period, as well as reducing the analgesic cost, since Nalbuphine esters have long-acting analgesic action. For example, the bioavailability of sebacoyl di-Nalbuphine ester is improved over that of Nalbuphine itself. Nalbuphine prodrugs also include Nalbuphine covalently linked to another pharmaceutical agent, for example via an amino acid. For example, Nalbuphine can be converted into a 3-acetylsalicylate (aspirin) derivative. Such duplex prodrugs including Nalbuphine provide a significant increase in the transdermal flux of drugs across human skin. Transdermal delivery of Nalbuphine and Nalbuphine pivalate from hydrogels by passive diffusion and iontophoresis (vide infra) has also been described. Therapeutic polymers such as polyesters and polyamides incorporating Nalbuphine, as well as polyNalbuphine derivatives can also be prepared. Controlled release of Nalbuphine prodrugs from biodegradable polymeric matrixes is influenced by prodrug hydrophilicity and polymer composition.

Pharmacokinetic and pharmacodynamic properties of Nalbuphine, its pharmaceutically acceptable salts, esters or other prodrugs can be further modulated by various delivery systems. For example, biodegradable polymeric microspheres for Nalbuphine prodrug controlled delivery have been described. Further, iontophoresis and electroporation enhance the transdermal delivery of Nalbuphine (NA) and two prodrugs, Nalbuphine benzoate (NAB) and sebacoyl di-Nalbuphine ester (SDN), when applied topically as solutions or hydrogels. Mucoadhesive buccal disks also provide for novel Nalbuphine prodrug controlled delivery.

In a further embodiment of the present invention, prodrugs of mu-opioid receptor antagonists and/or kappa-opioid receptor agonists and/or other dual-action μ-opioid receptor antagonist/κ-opioid receptor agonist compounds, including Butorphanol, Pentazocine, Nalorphine, Naltriben, Alazocine, Atomoxetine, Bremazocine, Salvinorin A, Samidorphan, Nalmefene, Nalodeine, and/or other therapeutic agents can be used either as individual therapeutic agents or in combination with any of the above for the treatment of dyskinesias.

The present invention represents a novel treatment option for those suffering from LID as well as other forms of dyskinesias including tardive dyskinesia, Huntington's chorea and Tourette's syndrome.

The compounds described herein can also be co-administered with other anti-dyskinetic drugs (e.g. amantadine, adenosine A2a antagonists, alpha-2 adrenergic antagonists (e.g. fipamezole)) and/or anti-Parkinson treatments (e.g. L-DOPA, dopamine agonists, monoamine oxidase (MAO) inhibitors (e.g. Safinamide), catechol-O-methyl transferase inhibitors, deep brain stimulation, etc.). Thus, a further embodiment of the invention encompasses a method of treating or mitigating a dyskinesia wherein a dual-action mu-antagonist/kappa-agonist or prodrug thereof is administered with another anti-Parkinson agent. Preferably the other anti-Parkinson agent is selected from the group consisting of L-DOPA, dopamine agonists, MAO inhibitors, COMT inhibitors, amantadine and anti-cholinergics. More preferably the other anti-Parkinson agent comprises L-DOPA. Most preferably the other anti-Parkinson agent is L-DOPA. Most preferably the dual-action mu-antagonist/kappa-agonist is Nalbuphine or a prodrug thereof, and the other anti-Parkinson agent is L-DOPA. Administration of either of the agents can be delayed by 0-12 hrs, preferably by 0-6 hours, and administration can be via the same or by a different route.

EXAMPLES

The present invention is described more fully by way of the following non-limiting examples. Modifications of these examples will be apparent to those skilled in the art. In order to target Nalbuphine for the treatment of Levodopa-induced dyskinesias, a major need for Parkinson's disease patients, its activity is confirmed in preclinical models and those data are used to guide dosing for human clinical trials.

Example 1: Assess Efficacy, Safety and Dosing of Nalbuphine in a Primate Model of L-DOPA Induced Dyskinesias Studies in primates are necessary to closely replicate the human condition and are used to fine tune the dosing and efficacy prior to a human clinical trial. The primate model of Parkinson's disease is a well established model that replicates the motor manifestations of the human disease, is responsive to PD therapeutics, and develops L-dopa-induced dyskinesia. Macaque monkeys (Macaca Fascicularis) are used in these studies, to which MPTP (1-methyl-4-phenyl-1,2,3,6-tetrahydropyridine; 0.5-0.8 mg/kg) is administered intravenously (iv) until a stable Parkinsonian state of moderate to severe degree develops. The animals are then adminis-tered oral levodopa/carbidopa (Sinemet 25/100) twice daily until stable dyskinesias are estab-lished. The response of animals to subcutaneous (SC) injections of levodopa methyl ester alone is then assessed, and the optimal dose established for each animal that results in moderate and reproducible dyskinesia. Levodopa methyl ester is routinely given with benserazide, a decarb-oxylase inhibitor to lessen the peripheral side effects of levodopa. Animals are then administered Nalbuphine SC, along with levodopa methyl ester plus benserazide to assess the effect of the combination on the severity and duration of dyskinesias. A minimum of 4 Nalbuphine doses and vehicle are administered in random order to ensure integrity of the studies, with the aim of finding a minimum efficacious dose and determining a viable dosing strategy for a future clinical trial. Each test dose including the vehicle is repeated 3 times. Monkeys are scored before L-DOPA administration and every 20 min interval thereafter for 3-4 hours. Tests are performed by trained observers in the morning after overnight fasting and repeated at intervals of at least 48 hr for drug washout. In addition to general clinical evaluation, a standardized scale for MPTP-treated primates to assess dyskinesias, the Klüver board test (motor task), and a scale assessing the nervous system (particularly alertness) is used. The examples described above identify efficacious doses of Nalbuphine that can be translated to human clinical trials.

Data

Macaques received iv MPTP to induce advanced Parkinsonism and were treated with chronic oral L-dopa/carbidopa to induce dyskinesia.

Example 1A

Figure 1:
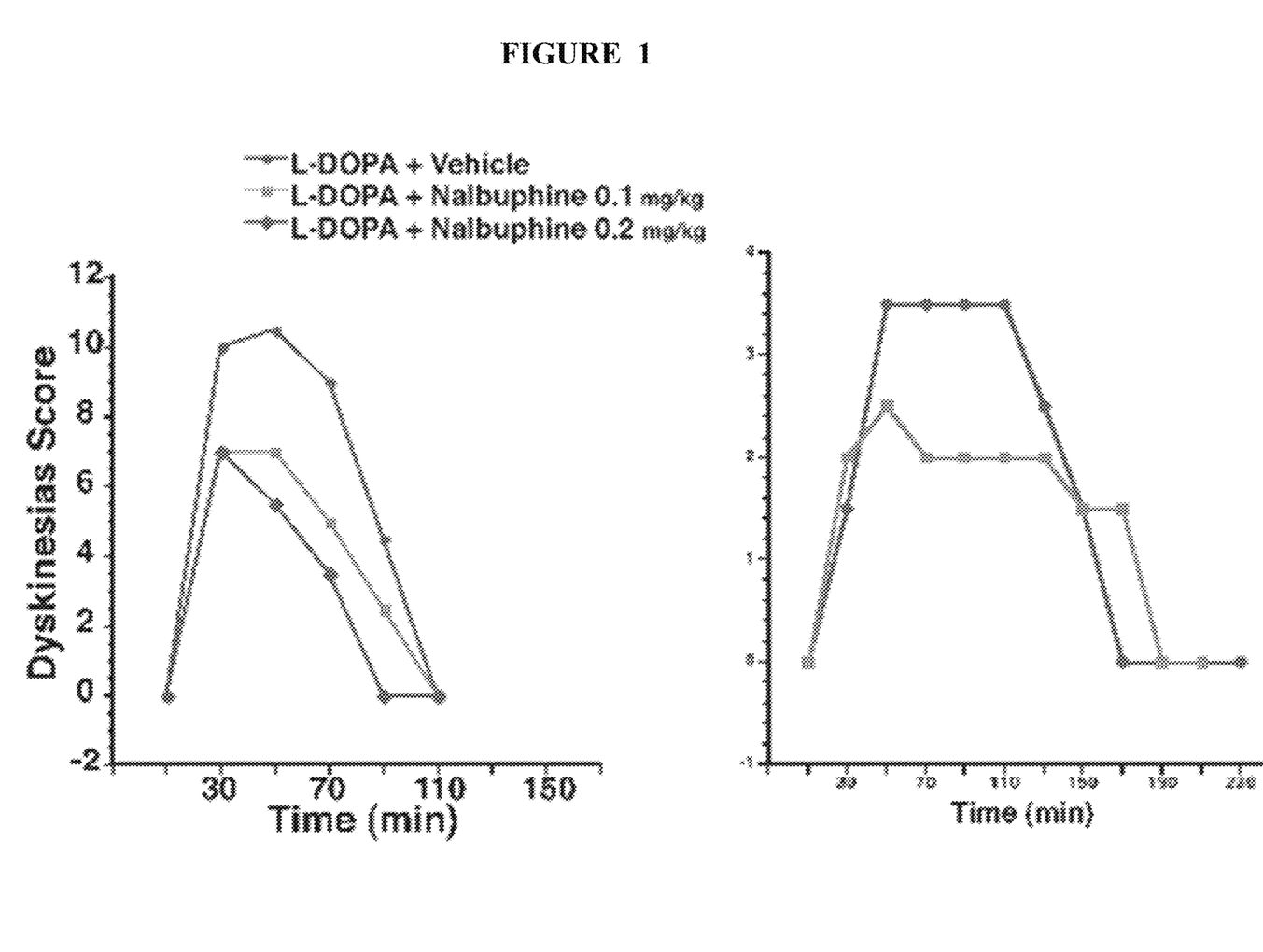
FIG. 1 displays graphs of dyskinesia score over time for two Parkinsonian monkeys treated with L-DOPA with and without Nalbuphine.

Nalbuphine was tested in two Parkinsonian monkeys with LID, at 0.1 mg/kg and 0.2 mg/kg given with 75 mg levodopa methyl ester (plus benserazide) all injected SC. Responses were evaluated with a motor disability scale for Parkinsonian monkeys including abnormal involuntary movements (PD-MDS). In both animals, dyskinesia severity was ameliorated and lasted for a shorter time when Nalbuphine was co-administered compared with levodopa administration alone (FIG. 1). No sedation occurred at these doses.

Example 1B

Figure 2:
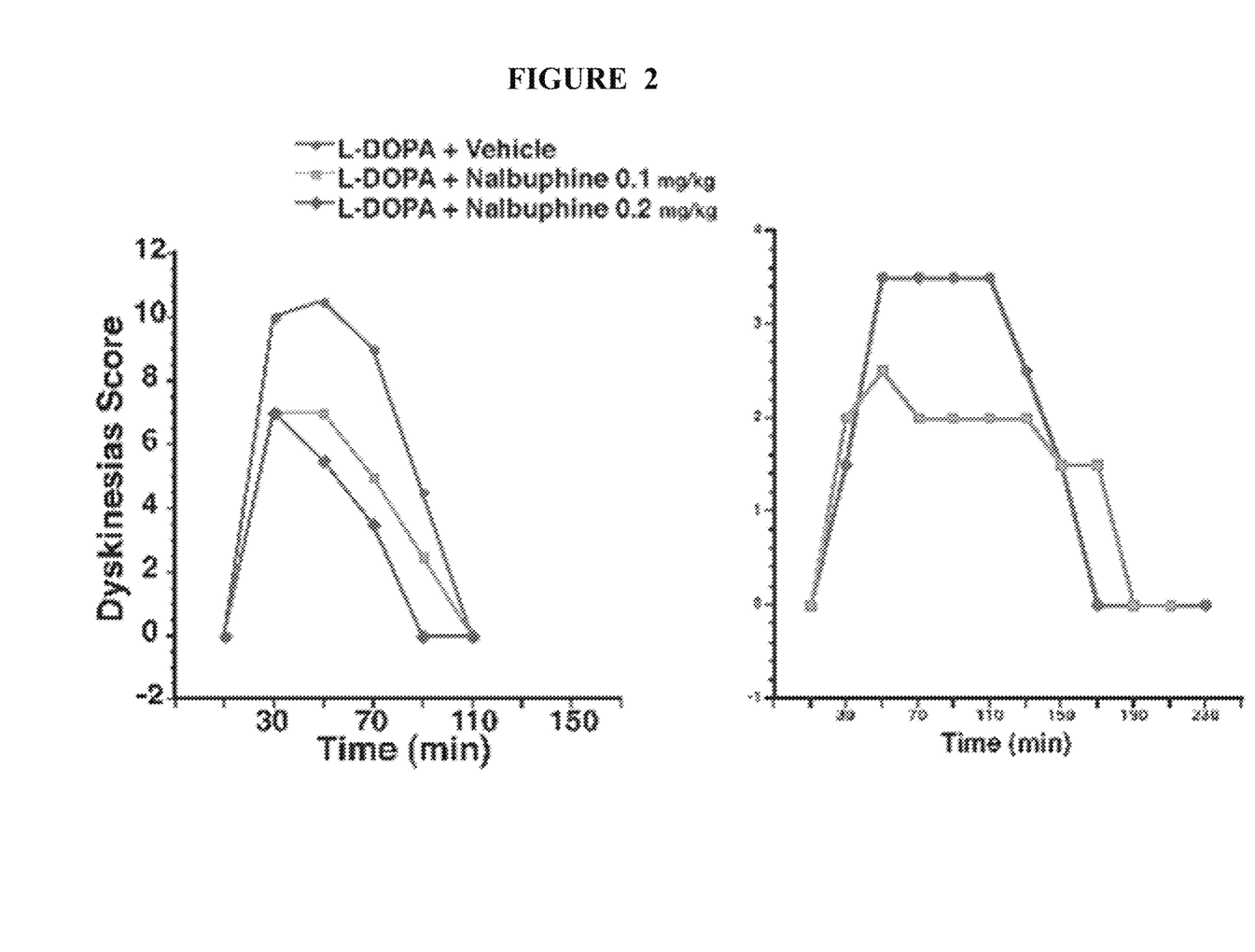
FIG. 2 displays a graph of dyskinesia score over time for three additional Parkinsonian monkeys treated with L-DOPA with and without Nalbuphine.

Three Parkinsonian monkeys with LID were tested. Animals were challenged with 75 mg SC injection of L-dopa methyl ester (plus benserazide) alone or immediately following SC Nalbuphine (0.25 mg/kg or 0.5 mg/kg), and responses were evaluated with a motor disability scale for Parkinsonian monkeys including abnormal involuntary movements. Each treatment was tested 2-3 times per animal. Error bars=S.E.M. Substantial reduction in the severity and duration of dyskinesias were noted with Nalbuphine co-administration. The effect of 0.5 mg/kg was slightly more pronounced than 0.25 mg/kg suggesting a dose-response effect (FIG. 2). Again, no sedation or other adverse effects were noted in these animals.

The foregoing examples and descriptions of the preferred embodiments are presented as illustrating, rather than as limiting the present invention as defined by the following claims. The present invention encompasses all variations and combinations of the features presented above, and are intended to be within the scope of the claims.

What is claimed is:

1. A method of treating or mitigating levodopa-induced dyskinesia in a subject diagnosed with Parkinson's disease, comprising administering a therapeutically effective amount of nalbuphine to a subject in need thereof, wherein the nalbuphine is in the form of a free base, or a pharmaceutically acceptable ester prodrug, or a pharmaceutically acceptable salt.

2. The method of claim 1, wherein the nalbuphine is in the form of a pharmaceutically acceptable salt.

3. The method of claim 1, wherein the nalbuphine is in the form of a pharmaceutically acceptable ester prodrug.

4. The method of claim 3, wherein the pharmaceutically acceptable ester prodrug is the benzoate ester of nalbuphine.

5. The method of claim 3, wherein the pharmaceutically acceptable ester prodrug is the sebacoyl diester of nalbuphine.

6. The method of claim 1, wherein from about 0.001 mg/kg to about 3 mg/kg of the nalbuphine is administered to the subject.

7. The method of claim 1, wherein the nalbuphine is administered to the subject in a non-injectable composition comprising:
(a) nalbuphine in the form of a free base, or a pharmaceutically acceptable ester prodrug, or a pharmaceutically acceptable salt and
(b) a pharmaceutically acceptable carrier.

8. The method of claim 7, wherein the composition is a tablet or a capsule.

9. The method of claim 1, wherein the nalbuphine is administered orally.

10. The method of claim 1, wherein the nalbuphine is administered by injection.

11. The method of claim 1, wherein the nalbuphine is administered by continuous infusion.

12. The method of claim 1, wherein the nalbuphine is administered to the subject in a non-injectable pharmaceutical composition selected from the group consisting of a tablet, a capsule, a syrup, a gel, a suppository, a skin patch, an inhalable powder, an inhalable aerosol, a sublingual spray, a sublingual solid dosage form, a buccal film, a mucoadhesive buccal patch, an intranasal spray, and an intranasal aerosol.

13. The method of claim 1, further comprising administering an anti-Parkinson agent.

14. The method of claim 13, wherein the anti-Parkinson agent is selected from the group consisting of levodopa, a dopamine agonist, a monoamine oxidase (MAO) inhibitor, a catechol-O-methyltransferase (COMT) inhibitor, amantadine and an anti-cholinergic.

15. The method of claim 14, wherein the anti-Parkinson agent is levodopa.

16. The method of claim 14, wherein the anti-Parkinson agent is a dopamine agonist.

17. The method of claim 14, wherein the anti-Parkinson agent is an MAO inhibitor.

18. The method of claim 14, wherein the anti-Parkinson agent is a COMT inhibitor.

19. The method of claim 14, wherein the anti-Parkinson agent is amantadine.

* * * * *